United States Patent [19]

Peyman et al.

[11] Patent Number: 5,242,908
[45] Date of Patent: Sep. 7, 1993

[54] USE OF BENZYLPHOSPHONIC ACID DERIVATIVES FOR THE TREATMENT OF DISEASES CAUSED BY VIRUSES

[75] Inventors: Anuschirwan Peyman, Brookline, Mass.; Eugen Uhlmann, Glashutten/Taunus, Fed. Rep. of Germany; Karlheinz Budt, Kelkheim/Taunus, Fed. Rep. of Germany; Jochen Knolle, Kriftel, Fed. Rep. of Germany; Irvin Winkler, Liederbach, Fed. Rep. of Germany; Matthias Helsberg, Kelkheim/Taunus, Fed. Rep. of Germany

[73] Assignee: Hoechst Aktiengesellschaft, Frankfurt am Main, Fed. Rep. of Germany

[21] Appl. No.: 648,622

[22] Filed: Feb. 1, 1991

[30] Foreign Application Priority Data

Feb. 2, 1990 [DE] Fed. Rep. of Germany ....... 4003054

[51] Int. Cl.$^5$ .................... A61K 31/66; C07F 9/40
[52] U.S. Cl. .................... 514/107; 514/110; 514/113; 514/120; 514/124; 514/129; 514/130; 514/132; 514/134; 514/135; 514/141; 558/86; 558/163; 558/178; 558/189; 558/192; 558/193; 558/197; 558/198; 558/214; 558/386; 562/8; 562/20
[58] Field of Search ............. 558/86, 163, 178, 189, 558/192, 193, 197, 198, 214, 386; 562/8, 20; 514/107, 110, 113, 120, 124, 129, 130, 132, 134, 135, 141

[56] References Cited

U.S. PATENT DOCUMENTS

| | | | |
|---|---|---|---|
| 3,161,667 | 12/1964 | Abramo et al. | 558/214 X |
| 3,363,032 | 1/1968 | Fitch | 558/214 |
| 3,385,688 | 5/1968 | Regel | 558/214 X |
| 3,538,196 | 11/1970 | Baranaukas et al. | 558/163 X |
| 3,555,123 | 1/1971 | Fischer et al. | 558/193 X |
| 3,867,484 | 2/1975 | Beriger | 558/193 X |
| 4,495,111 | 1/1985 | Guerin et al. | 558/214 X |

FOREIGN PATENT DOCUMENTS

| | | |
|---|---|---|
| 192327 | 8/1986 | European Pat. Off. |
| 3001065A1 | 7/1981 | Fed. Rep. of Germany |
| 2358882 | 2/1978 | France |
| 2449097 | 9/1980 | France |
| 2022589 | 12/1979 | United Kingdom |
| 2165153 | 4/1986 | United Kingdom |

OTHER PUBLICATIONS

Okamoto et al, Abstract 408015, Index Chemicis, vol. 107, Issue 1248 (1987).

(List continued on next page.)

*Primary Examiner*—Richard L. Raymond
*Attorney, Agent, or Firm*—Finnegan, Henderson, Farabow, Garrett & Dunner

[57] ABSTRACT

The use of a compound of the formula I

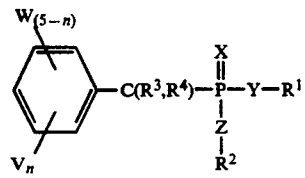

in which V is an alkyl group, fluorine, chlorine, bromine, or iodine, n is an integer from 1 to 5, W is an alkyl, alkenyl, alkynyl or alkoxy group, cyanide, nitro, carboxyl, hydrogen or a cycloalkyl, aryl, aralkyl or carboalkoxy group, $R^1$ and $R^2$ are an alkyl, alkenyl, alkynyl, cycloalkyl or halogenoalkyl group, sodium, potassium, calcium, magnesium, aluminum, lithium, ammonium, triethylammonium or hydrogen, $R^1$ and $R^2$ together form a cyclic diester, $R^3$ and $R^4$ are an alkyl, alkenyl, alkynyl, carboalkoxy, cycloalkyl or alkoxy group, hydrogen, fluorine, chlorine, bromine or iodine and X, Y and Z are oxygen or sulfur, for the treatment of diseases caused by DNA viruses or RNA viruses is described.

4 Claims, No Drawings

OTHER PUBLICATIONS

Bellucci et al, Chemical Abstracts, vol. 114 (1991) 62187x.
Terada et al, Chemical Abstracts, vol. 112 (1990) 235189p.
Ricoh Co., Chemical Abstracts, vol. 102 (1985) 26396h.
Tedjamulia et al, Chemical Abstracts, vol. 102 (1985) 24403j.
Arient et al, Chemical Abstracts, vol. 101 (1984) 230161m.
Sasaki et al, Chemical Abstracts, vol. 101 (1984) 219792x.
Gourse, Chemical Abstracts, vol. 96 (1982) 64203h.
Arient, Chemical Abstracts, vol. 95 (1981) 61703q.
Minagawa et al, Chemical Abstracts, vol. 94 (1981) 85140j.
Minagawa et al, Chemical Abstracts, vol. 93 (1980) 240630u.
Motonubu et al, Chemical Abstracts, vol. 93 (1980) 133415f.
Motonobu et al, Chemical Abstracts, vol. 91 (1979) 108685v.
Ernst, Chemical Abstracts, vol. 87 (1977) 101461c.
Molchanova et al, Chemical Abstracts, vol. 74 (1971) 147037d.
Zhuravleva et al, Chemical Abstracts, vol. 69 (1968) 27484x.
Griffin et al, Chemical Abstracts, vol. 67 (1967) 77731e.
Siddall et al, Chemical Abstracts, vol. 57 (1962) 15142f.
R. W. Sidwell et al., "Effect of phosphonic acid analogs of acyclovir and ganciclovir on in vitro cytomegalovirus infections", Nucleosides & Nucleotides, vol. 8, Nr. 5&6, 1989, pp. 833–836.
N. D. L'Viv et al., "Antiherpes activity of phosphonic acid derivatives and their combinations with interferon inducers on the model of eye herpes", Chemical Abstracts, vol. 111, Nr. 5, Jul. 31, 1989, p. 19, Nr. 33158w, Columbus, Ohio, U.S.
P. M. Malykhin et al., "The effectiveness of domestic aynthetic preparations in protecting strawberries from viral infections", Biological Abstract, No. 86128890, (1988).
C-P. Yang and T-M. Lee, "Syntheses and Properties of 4-Hydroxy-3, 5-Dibromobenzyl Phosphonates and Their Flame-Retarding Effects on ABS Polymer," J. Polymer Sci.: Part A: Polymer Chem., 27:2239–2251 (1989).
C. Bellucci, F. Gualtieri, S. Scapecchi, E. Teodori, "Negative Inotropic and Calcium Antagonistic Activity of Alkyl and Arylalkyl Phosphonates," Il Farmaco, 44 (12):1167–1191 (1989).
C. Bellucci, F. Gualtieri, A. Chiarini, "Negative inotropic activity of para-substituted diethyl benzylphosphonates related to fosedil," Eur. J. Med. Chem., 22:473–477 (1987).
J. Mao, E. Otis, A von Esch, T. Herrin, J. Fairgrieve, N. Shipkowitz, R. Duff, "Structure-Activity Studies on Phosphonoacetate," Antimicrobil Agents and Chemotherapy, 27 (2):197–202 (1985).
B-R. Liaw, W-J. Guo, "Synthesis of Some Dialkyl Bromo-Substituted Benzyl Phosphonates," J. Chim. Chem. Soc., 31:311–314 (1984).
Linn, Tetracyanoethylene Oxide. III. Mechanism of the Addtion to Olefins, Journal of the American Chemical Society, 87 (1965), pp. 3665–3672.

USE OF BENZYLPHOSPHONIC ACID DERIVATIVES FOR THE TREATMENT OF DISEASES CAUSED BY VIRUSES

Benzylphosphonic acids have already been described. According to information in the literature, benzylphosphonic acids are used as intermediate products for the preparation of optical brighteners or as flameproofing agents (German Offenlegungsschrift 3,001,065; J. Chin. Chem. Soc., 31, 1984, page 311; and J. Polymer Sci., Part A, 27, 1989, page 2239).

Benzylphosphonic acid derivatives have not been described as compounds having an antiviral action (J. C. H. Mao et al., Antimicrob. Agents Chemother. 27, 1985, page 197).

Surprisingly, it has now been found that halogenobenzylphosphonic acid derivatives or alkylbenzylphosphonic acid derivatives have an antiviral activity.

The invention thus relates to:

1. A compound of the formula I

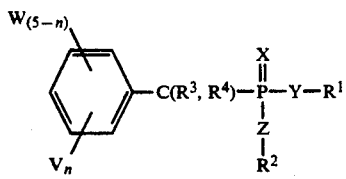

in which

V is a straight-chain or branched alkyl group having 1 to 4 carbon atoms, fluorine, chlorine, bromine, iodine or hydrogen, n is an integer from 1 to 5, W is a straight-chain or branched alkyl group having 1 to 20 carbon atoms, a straight-chain or branched alkenyl or alkynyl group having 2 to 20 carbon atoms, an aralkyl group having 7 to 20 atoms, a cycloalkyl group having 3 to 8 carbon atoms, a straight-chain or branched alkoxy group having 1 to 10 carbon atoms, an aryl group having 6, 10 or 14 carbon atoms or an alkyl group having 1 to 4 carbon atoms, substituted by one or more substituents from the group comprising the radical of the formula

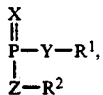

the radical of the formula —COOR$^6$ or halogen, in which halogen is chlorine, bromine, iodine or fluorine, a fused-on aromatic, which can be substituted by an alkyl group having 1 to 4 carbon atoms, cyanide, nitro or hydrogen, or is the radical of the formula Ia, —COOR$^6$  Ia in which R$^6$ is a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, sodium, potassium, calcium, magnesium, aluminum, lithium, ammonium, triethylammonium, hydrogen or a straight-chain or branched halogenoalkyl group having 1 to 20 carbon atoms, in which halogen is chlorine, bromine, iodine or fluorine, R$^1$ and R$^2$, which can be identical or different, are a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, sodium, potassium, calcium, magnesium, aluminum, lithium, ammonium, triethylammonium, hydrogen or a straight-chain or branched halogenoalkyl group having 1 to 20 carbon atoms, in which halogen is chlorine, bromine, iodine or fluorine, or R$^1$ and R$^2$ together form a cyclic diester having 2 to 6 carbon atoms in the ring, R$^3$ and R$^4$, which can be identical or different, are a straight-chain or branched alkyl group having 1 to 20 carbon atoms, a straight-chain or branched alkynyl or alkenyl group having 2 to 20 carbon atoms, a cycloalkyl group having 3 to 8 carbon atoms, an aralkyl group having 7 to 20 carbon atoms, a straight-chain or branched alkoxy group having 1 to 10 carbon atoms, hydrogen, fluorine, chlorine, bromine or iodine, or are the radical of the formula Ib —COOR$^7$  Ib in which R$^7$ is a straight-chain or branched alkyl group having 1 to 4 carbon atoms and X, Y and Z, which can be identical or different, are oxygen or sulfur, as a pharmaceutical.

2. The use of the compound of the formula I for the preparation of a pharmaceutical for the treatment of diseases caused by DNA viruses or RNA viruses.

The term alkyl group having 1 to 10 carbon atoms is to be understood as meaning, for example, the following radicals: methyl, ethyl, propyl, isopropyl, n-butyl, sec.-butyl, tert.-butyl, 2,2-dimethyl-1-propyl, n-pentyl, n-hexyl, n-heptyl, n-octyl, n-nonyl and n-decyl. By the term alkenyl group having 2 to 10 carbon atoms is meant, for example, the following radicals: ethenyl, propenyl, butenyl, n-pentenyl, n-hexenyl, n-heptenyl, n-octenyl, n-nonenyl or n-decenyl. By the term alkynyl group having 2 to 10 carbon atoms is meant, for example, the following radicals: ethynyl, propynyl, butynyl, n-pentynyl, n-hexynyl, n-heptynyl, n-nonynyl, n-octynyl or n-decynyl. An aralkyl group having 7 to 16 carbon atoms is to be understood as meaning, for example, the following radicals: phenylmethyl, phenylethyl, phenylbutyl, phenylpropyl, phenylpentyl, phenylhexyl, phenylheptyl, phenyloctyl, phenylnonyl or phenyldecyl. A cycloalkyl group having 3 to 8 carbon atoms is to be understood as meaning radicals such as cyclopropyl, cyclobutyl, cyclopentyl, cyclohexyl, cycloheptyl or cyclooctyl. Alkoxy groups having 1 to 4 carbon atoms are, for example, radicals such as methoxy, ethoxy, propoxy, isopropoxy, n-butoxy, sec.-butoxy or tert.-butoxy. Aryl groups having 6, 10 or 14 carbon atoms are, for example, radicals such as phenyl, naphthyl, anthryl or phenanthryl. Fused-on aromatics are, for example, radicals which, together with the phenyl group of the formula I, form radicals such as naphthyl, anthryl or phenanthryl.

A compound of the formula I in which

V is bromine, hydrogen or methyl, n is an integer from 1 to 5,

W is methoxy or hydrogen, $R^1$ and $R^2$, which can be identical or different, are a straight-chain or branched alkyl group having 1 to 10 carbon atoms, an alkenyl or alkynyl group having 2 to 10 carbon atoms, an aralkyl group having 7 to 16 carbon atoms or hydrogen, $R^3$ and $R^4$, which can be identical or different, are a straight-chain or branched alkyl group having 1 to 4 carbon atoms, an alkenyl or alkynyl group having 2 to 10 carbon atoms, a straight-chain or branched alkoxy group having 1 to 4 carbon atoms, hydrogen, fluorine, chlorine or bromine, or are the radical of the formula Ib $$-COOR^7 \qquad \text{Ib}$$

in which $R^7$ is a straight-chain or branched alkyl group having 1 to 4 carbon atoms and X, Y and Z are oxygen,
is preferred.

The compound of the formula I is prepared by reaction of the compound of the formula II

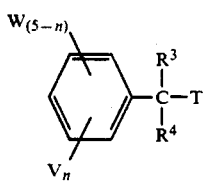

in which

V is a straight-chain or branched alkyl group having 1 to 4 carbon atoms, fluorine, chlorine, bromine, iodine or hydrogen, n is an integer from 1 to 5, W is a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, a straight-chain or branched alkoxy group having 1 to 10 carbon atoms, an aryl group having 6, 10 or 14 carbon atoms, an alkyl group having 1 to 4 carbon atoms, substituted by one or more substituents from the group comprising the radical of the formula

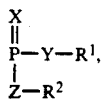

the radical of the formula $-COOR^6$ or halogen, in which halogen is chlorine, bromine, iodine or fluorine, a fused-on aromatic, which can be substituted by an alkyl group having 1 to 4 carbon atoms, cyanide, nitro or hydrogen, or is the radical of the formula Ia $$-COOR^6 \qquad \text{Ia}$$

in which $R^6$ is a straight-chain or branched alkyl group having 1 to 20 carbon atoms, a straight-chain or branched alkenyl, or alkynyl group having 2 to 20 carbon atoms, an aralkyl group having 7 to 20 carbon atoms, a cycloalkyl group having 3 to 8 carbon atoms, sodium, potassium, calcium, magnesium, aluminum, lithium, ammonium, triethylammonium, hydrogen or a straight-chain or branched halogenoalkyl group having 1 to 20 carbon atoms, in which halogen is chlorine, bromine, iodine or fluorine, T is chlorine, bromine, iodine, methylsulfonyl, phenylsulfonyl or tosylsulfonyl and $R^3$ and $R^4$, which can be identical or different, are a straight-chain or branched alkyl group having 1 to 20 carbon atoms, a straight-chain or branched alkynyl or alkenyl group having 2 to 20 carbon atoms, a cycloalkyl group having 3 to 8 carbon atoms, an aralkyl group having 7 to 20 carbon atoms, a straight-chain or branched alkoxy group having 1 to 10 carbon atoms, hydrogen, fluorine, chlorine, bromine or iodine, or are the radical of the formula Ib $$-COOR^7 \qquad \text{Ib}$$

in which $R^7$ is a straight-chain or branched alkyl group having 1 to 4 carbon atoms, with the compound of the formula III

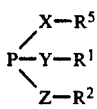

in which $R^1$ and $R^2$, which can be identical or different, are a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, sodium, potassium, calcium, magnesium, aluminum, lithium, ammonium, triethylammonium, hydrogen or a straight-chain or branched halogenoalkyl group having 1 to 20 carbon atoms, in which halogen is chlorine, bromine, iodine or fluorine, or $R^1$ and $R^2$ together form a cyclic diester having 2 to 6 carbon atoms in the ring, $R^5$ is a straight-chain or branched alkyl group having 1 to 4 carbon atoms and X, Y and Z, which can be identical or different, are oxygen or sulfur.

The compound of the formula I is synthesized by reaction of the compound of the formula II with the compound of the formula III, advantageously at temperatures between 100° and 250° C., by a method analogous to methods which have been described (U.S. Pat. No. 4,299,615; Houben-Weyl, Methoden der Org. Chemie (Methods of Organic Chemistry), Volume XII/1, page 423, Thieme Verlag Stuttgart; and Houben-Weyl, Methoden der Org. Chemie (Methods of Organic Chemistry), Volume E2, page 300). The reaction can be carried out in a suitable solvent, such as hexamethylphosphoric acid amide (HEMPA), dimethylformamide (DMF), dimethyl sulfoxide (DMSO), N,N'-dimethyl-N,N'-propyleneurea (DMPU) or N,N'-dimethyl-N,N'-ethyleneurea (DMEU). The reaction can also be carried out without a solvent.

Purification is carried out by generally customary methods, preferably by chromatography over silica gel using suitable mobile phases, by distillation or by recrystallization from suitable solvents.

Compounds of the formula I can furthermore be prepared from other compounds of the formula I by generally known chemical modification, such as, for example, electrophilic aromatic substitution or oxidation of alkyl side chains.

The compounds of the formula II and formula III can be prepared by known methods. The conversion of the phosphonic acid diesters into their monoesters and into the corresponding free acids or salts thereof is carried out, for example, by boiling with dilute hydrochloric acid (Houben-Weyl, Methoden der Oganischen Chemie (Methods of Organic Chemistry), Volume XII/1, 1963, page 423) or by reaction with trimethylbromosilane (C. E. McKenna, J. Schmidhauser, J.C.S. Chem. Commun., 1979, Page 739). Purification is carried out by recrystallization in suitable solvents or by chromatographic methods, preferably by ion exchange chromatography using suitable mobile phases.

The desired salt forms can also be obtained by ion exchange chromatography.

The compound of the formula I has useful pharmacological properties, in particular an antiviral action, and in particular against diseases caused both by DNA viruses and by RNA viruses, especially against diseases caused by herpes simplex virus (HSV 1), myxoviruses, Friend leukemia virus (FLV) or human immunodeficiency virus (HIV). The compounds according to the invention are thus suitable for combating various diseases caused by viruses, such as disease of the respiratory tract, diseases of the skin, eye and central nervous system, AIDS and AIDS-related states, such as AIDS-related complexes (ARC), generalized lymphadenopathy (PGL), AIDS-related neuralgic states (such as mental deficiency or tropical paraperesis), anti-HIV antibody-positive states, Kaposi's sarcoma or thrombopenic purpura.

A test of the efficacy of chemotherapeutics for HIV infections on human presents difficulties, since as yet no infection model exists in laboratory animals. Infection with other retroviruses must therefore be resorted to for testing chemotherapeutics. In this case, infection of the mouse with the Friend leukemia virus was chosen. For this test, normal NMRI laboratory mice (NMRI=Naval Medical Research Institute) were infected, by intravenous injection, with mouse serum containing Friend leukemia virus. In the untreated control animals, a significant enlargement of the spleen and liver developed as a symptom of the infection within 2 weeks. Treatment was performed over 10 days, starting 48 hours after the infection. The animals were sacrificed and opened up on the 14th day of the experiment. The spleen was removed and weighed. The spleen weight of the treated animals was compared with that of the untreated infection control as a measurement parameter of the therapeutic efficacy. In non-infected adult laboratory mice (20-24 g body weight), the spleen reached about 1% of the body weight or less, whereas in infected animals the spleen weighed about 10% of the body weight at the end of the experiment.

The compound of the formula I can be used as a pharmaceutical either by itself or as a mixture with physiologically tolerated auxiliaries or excipients. For this purpose, it can be administered orally in a dose of 1 to 500 mg/kg/day, preferably 5 to 50 mg/kg/day. It is administered for parenteral, rectal or topical use or as an aerosol in an amount of 0.5 to 500 mg/kg/day, preferably 2 to 100 mg/kg/day. The compound of the formula I is advantageously administered in dosage units which contain at least the effective amount of the compounds according to the invention, preferably 25 to 6000 mg, particularly preferably 100 to 1000 mg. These values relate to an adult human weighing 75 kg. These dosage units can also be administered several times per day. In severe cases, the dosage can also be increased. In many cases, however, smaller amounts are also adequate. The following compounds are particularly suitable for combating diseases caused by RNA viruses or DNA viruses:

dimethyl 2-methylbenzylphosphonate,
diethyl 3-bromobenzylphosphonate,
diethyl 2-bromobenzylphosphonate,
diethyl 4-bromobenzylphosphonate,
diethyl 2-methyblenzylphospnonate,
diethyl 3-methylbenzylphosphonate,
diethyl 4-methylobenzylphosphonate,
diethyl 2-fluorobenzylphosphonate,
diethyl 2-chlorobenzylphosphonate,
diethyl 2,5-dimethylbenzylphosphonate,
diisopropyl 2-methylbenzylphosphonate,
di-n-butyl 2-methylbenzylphosphonate,
di-(2-chloroethyl) 2-methylbenzylphosphonate,
di-triethylammonium 2-methylbenzylphosphonate,
diethyl 4-chlorobenzylphosphonate,
diethyl 2-iodobenzylphosphonate,
diethyl 4-fluorobenzylphosphonate,
diisopropyl 4-iodobenzylphosphonate,
diethyl 2-nitrobenzylphosphonate,
diethyl 2-phenylethylphosphonate,
diethyl 2-carboxyethylbenzylphosphonate,
diethyl 3-carboxymethylbenzylphosphonate,
diethyl 2-(ethylacetyl)benzylphosphonate,
diethyl 4-methoxybenzylphosphonate,
diethyl 2-methyl-4-bromobenzylphosphonate,
diethyl 4-trifluoromethylbenzylphosphonate,
1,2-phenylene-bis-(diethyl methylphosphonate),
1,3-phenylene-bis-(diethyl methylphosphonate),
diethyl 2-carboxybenzylphosphonate,
2-carboxybenzylphosphonic acid,
di-triethylammonium 2-carboxyethylbenzylphosphonate,
diethyl 1-methylnaphthylphosphonate,
diethyl 2-methylnaphthylphosphonate,
diethyl 2-cyanobenzylphosphonate,
diethyl 4-cyanobenzylphosphonate and
2-methylbenzylphosphonic acid.

The compound of the formula I according to the invention can also be administered in combination with other active compounds, in particular antiviral agents and immunostimulators, such as interferons. The invention furthermore relates to the use of the compound of the formula I according to the invention in the preparation of pharmaceuticals which are employed for the treatment and prophylaxis of the abovementioned diseases. The invention furthermore relates to pharmaceuticals containing one or more compounds of the formula I according to the invention.

The pharmaceuticals are prepared by processes which are known per se and familiar to the expert. As pharmaceuticals, the compound of the formula I according to the invention is employed either as such or preferably in combination with suitable pharmaceutical auxiliaries or excipients, in the form of tablets, coated tablets, capsules, suppositories, emulsions, suspensions or solutions, the active compound content being up to about 95%, advantageously between 10% and 75%.

Suitable auxiliaries and excipients for the desired pharmaceutical formulation are, for example, in addition to solvents, gel-forming agents, suppository bases, tablet auxiliaries and other active compound carriers, also antioxidants, dispersing agents, emulsifiers, foam suppressnats, flavor correctants, preservatives, solubilizing agents or dyestuffs.

The compound of the formula I can be administered orally, parenterally, intravenously or rectally, intranasal administration as an aerosol being particularly preferred, in addition to oral administration.

For an oral use form, the compound of the formula I is mixed with the additives suitable for this purpose, such as excipients, stabilizers or inert diluents, and the mixture is brought into suitable presentation foams, such as tablets, coated tablets, push-fit capsules or aqueous or oily solutions, by the customary methods. Inert excipients which can be used are, for example, gum arabic, magnesia, magnesium carbonate, potassium phosphate, lactose, glucose or starch, in particular cornstarch. Formulation can be carried out here either as dry granules or as moist granules. Possibly oily excipients or solvents are, for example, vegetable or animal oils, such as sunflower oil or cod-liver oil.

For subcutaneous or intravenous administration, the compound of the formula I is dissolved, suspended or emulsified with the substances suitable for this purpose, such as solubilizing agents, emulsifiers or other auxiliaries. Possible solvents are, for example, physiological saline solution, alcohols, for example ethanol, propanol or glycerol, sugar solutions, such as glucose solutions or mannitol solutions, or a mixture of solvents.

The following examples serve to illustrate the invention further.

EXAMPLE 1

Preparation of dimethyl 2-methylbenzylphosphonate (A)

34.6 g (0.19 mol) of 2-methylbenzyl bromide and 23.2 g (0.19 mol) of trimethyl phosphite were heated to 105° C. for 3 hours. The methyl bromide formed was collected in a cold trap at −70° C. The product was purified by fractional distillation.

Yield: 22.5 g (57%); boiling point: 106° C./0.4 mm; $^1$H-NMR (60 MHz, CDCl$_3$/TMS); $\delta$=2.33 (s,3H,Ar—CH$_3$), 3.22 (d,2H, CH$_2$—P) $J_{PH}$=22 Hz, 3.66 (d,6H,P—O—CH$_3$), 7.26 (s-broad, 4H,Ar—H).

EXAMPLE 2

Preparation of diethyl 3-bromobenzylphosphonate (B)

50 g (0.2 mol) of 3-bromobenzyl bromide and 33.2 g (0.2 mol) of triethyl phosphite were heated at 140° C. for 2 hours, during which ethyl bromide was distilled off. The product was distilled over a 30 cm Vigreux column.

Yield: 44.02 g (72%); boiling point: 140°–148° C./0.7–0.8 mm;
$^1$H-NMR (60 MHz, CDCl$_3$/TMS): $\delta$=1.21 (t,6H,P—O—CH$_2$—CH$_3$), 3.10 (d,2H,CH$_2$—P) $J_{PH}$=22 Hz, 4.03 (dq,4H,P—O—CH$_2$—CH$_3$), 7.04–7.61 (m,4H,Ar—H).

EXAMPLE 3

Preparation of diethyl 2-bromobenzylphosphonate (C)

The process is as in Example 2. 2-Bromobenzyl bromide was used instead of 3-bromobenzyl bromide.
Yield: 78%; boiling point: 120° C./0.2 mm;
$^1$H-NMR (60 MHz, CDCl$_3$/TMS): $\delta$=1.25 (t,6H,P—O—CH$_2$—CH$_3$), 3.4 (d,2H,CH$_2$—P) $J_{PH}$=22 Hz, 4.06 (dq,4H,P—O—CH$_2$—CH$_3$), 7.06–7.70 (m,4H,Ar—H)

EXAMPLE 4

Preparation of diethyl 4-bromobenzylphosphonate (D)

The process as in Example 2. 4-Bromobenzyl bromide was used instead of 3-bromobenzyl bromide.
Yield: 66%; boiling point: 135° C./0.3 mm; $^1$H-NMR (60 MHz, CDCl$_3$/TMS); $\delta$=1.23 (t,6H,P—O—CH$_2$—CH$_3$), 3.10 (d,2H,CH$_2$—P) $J_{PH}$=22 Hz, 4.03 (dq,4H,P—O—CH$_2$—CH$_3$), 6.99–7.62 (m,4H,Ar—H)

EXAMPLE 5

Preparation of diethyl 2-methylbenzylphosphonate (E)

The process is as in Example 2. 2-Methylbenzyl bromide was used instead of 3-bromobenzyl bromide.
Yield: 75%; boiling point: 122° C. C/4 mm; $^1$H-NMR (270 MHz, CDCl$_3$/TMS): $\delta$=1.25 (t,6H,P—O—CH$_2$—CH$_3$), 2.39 (s,3H,Ar—CH$_3$), 3.18 (d,2H,CH$_2$—P) $J_{PH}$=24 Hz, 4.00 (dq,4H,P—O—CH$_2$—CH$_3$), 7.10–7.31 (m,4H,Ar—H).

EXAMPLE 6

Preparation of diethyl 3-methylbenzylphosphonate (F)

The process is as in Example 2. 3-Methylbenzyl bromide was used instead of 3-bromobenzyl bromide.
Yield: 84%; boiling point: 108° C./0.2 mm; $^1$H-NMR (60 MHz, CDCl$_3$/TMS); $\delta$=1.21 (t,6H,P—O—CH$_2$—CH$_3$), 2.30 (s,3H,Ar—CH$_3$), 3.13 (d,2H,CH$_2$—P) $J_{PH}$=22 Hz, 4.03 (dq,4H,P—O—CH$_2$—CH$_3$), 7.13 (s-broad, 4H,Ar—H).

EXAMPLE 7

Preparation of diethyl 4-methylbenzylphosphonate (G)

The process is as in Example 2. 4-Methylbenzyl bromide was used instead of 3-bromobenzyl bromide.
Yield: 83%; boiling point: 110°–115° C./0,15 mm; $^1$H-NMR (60 MHz, CDCl$_3$/TMS): $\delta$=1.22 (t,6H,P—O—CH$_2$—CH$_3$), 2.35 (s,3H,Ar—CH$_3$), 3.10 (d,2H,CH$_2$—P) $J_{PH}$=22 Hz, 4.03 (dq,4H,P—O—CH$_2$—CH$_3$), 7.15 (s,4H,Ar—H).

EXAMPLE 8

Preparation of diethyl 2-fluorobenzylphosphonate (H)

The process is as in Example 2. 2-Fluorobenzyl bromide was used instead of 3-bromobenzyl bromide.
Yield: 83%; boiling point: 105°–114° C./0.6 mm; $^1$H-NMR (60 MHz, CDCl$_3$/TMS): $\delta$=1.23 (t,6H,P—O—CH$_2$—CH$_3$), 3.20 (d,2H,CH$_2$—P) $J_{PH}$=22 Hz, 4.02 (dq,4H,P—O—CH$_2$—CH$_3$), 6.85–7.70 (m,4H,Ar—H).

EXAMPLE 9

Preparation of diethyl 2-chlorobenzylphosphoante (I)

The process is as in Example 2. 2-Chlorobenzyl bromide was used instead of 3-bromobenzyl bromide.
Yield: 68%; boiling point: 140°–145° C./0.002 mm; $^1$H-NMR (60 MHz, CDCl$_3$/TMS); $\delta$=1.20 (t,6H, P—O—CH$_2$—CH$_3$), 3.38 (d,2H,CH$_2$—P) $J_{PH}$=22 Hz, 4.02 (dq,4H, P—O—CH$_2$—CH$_3$), 7.00–7.65 (m,4H,Ar—H)

EXAMPLE 10

Preparation of diethyl 2,5-dimethylbenzylphosphonate (K)

The process is as in Example 2. 2,5-Dimethylbenzyl bromide was used instead of 3-bromobenzyl bromide.

Yield: 80%; boiling point: 116° C./0.2 mm; $^1$H-NMR (60 MHz, CDCl$_3$/TMS): $\delta = 1.29$ (t,6H,P—O—CH$_2$—CH$_3$), 2.34 (s,6H,Ar—CH$_3$), 3.20 (d,2H,CH$_2$—P) $J_{PH} = 22$ Hz, 4.05 (dq, 4H, P—O—CH$_2$—CH$_3$), 7.07 (s-broad, 4H, Ar—H)

EXAMPLE 11

Preparation of diisopropyl 2-methylbenzylphosphonate (L)

34.5 g (0.19 mol) of 2-methylbenzyl bromide and 39 g (0.19 mol) of triisopropyl phosphite were heated at 150° C. for 2 hours. During this procedure, i-propyl bromide distilled off. The product was distilled through a 30 cm Vigreux column.

Yield: 78%; boiling point: 110° C./0.35 mm; $^1$H-NMR (60 MHz, CDCl$_3$/TMS): $\delta = 1.26$ (t,6H,P—O—CH(CH$_3$)$_2$), 2.37 (s,3H,Ar—CH$_3$), 3.13 (d,2H,CH$_2$—P) $J_{PH} = 22$ Hz, 4.56 (dhep,2H,P—O—CH(CH$_3$)$_2$), 7.15 (s-broad, 4H, Ar—H).

EXAMPLE 12

Preparation of di-n-butyl 2-methylbenzylphosphonate (M)

34.5 g (0.19 mol) of 2-methylbenzyl bromide and 46.8 g (0.19 mol) of tri-n-butyl phosphites were heated at 160° C. for 2 hours. During this procedure, n-butyl bromide distilled off. The product was distilled as in Example 11.

Yield: 55%; boiling point: 143° C./0.5 mm; $^1$H-NMR (6-0 MHz, CDCl$_3$/TMS): $\delta = 0.64$–1.77 (m,14H,CH$_2$—CH$_2$—CH$_3$), 2.39 (s,3H,Ar—CH$_3$), 3.18 (d,2H,CH$_2$—P) $J_{PH} = 22$ Hz, 3.95 (dt,4H,P—O—CH$_2$—), 7.20 (s-broad, 4H, Ar—H)

EXAMPLE 13

Preparation of di-(2-chloroethyl) 2-methylbenzylphosphonate (N)

34.5 g (0.19 mol) of 2-methylbenzyl bromide and 50.4 g (0.19 mol) of tri-(2-chloroethyl) phosphites were heated at 160° C. for 2 hours. During this procedure, 1-bromo-2-chloroethane distilled off. The product was distilled as in Example 11.

Yield: 92%; boiling point: 170° C./0.5 mm; $^1$H-NMR (60 MHz, CDCl$_3$/TMS): $\delta = 2.41$ (s,3H,Ar—CH$_3$), 3.29 (d,2H,CH$_2$—P) $J_{PH} = 22$ Hz, 3.59 (m,4H,O—CH$_2$—CH$_2$—Cl) 4.18 (m,4H,O—CH$_2$—CH$_2$—Cl), 7.11–7.33 (m,4H,Ar—H)

EXAMPLE 14

Preparation of di-triethylammonium 2-methylbenzylphosphonate (O)

3.2 g (21 mmol) of trimethylsilyl bromide were added dropwise to 2 g (9.3 mmol) of the compound (E) in 10 ml of absolute dioxane and the reaction mixture was heated to 50° C. and stirred at this temperature for 6 hours. It was evaporated, and the residue was treated with water and lyophilized several times. The crude product was purified by chromatography over DEAE ®Sephadex A25 (Et$_3$NH$^+$ form, Pharmacia, Freiburg, FRG) and elution with a triethylammonium bicarbonate gradient of 0.3–1.0M.

Yield: 1.21 g (61%); oil; $^1$H-NMR (60 MHz, DMSO/TMS): $\delta = 1.28$ (t,18H,N—CH$_2$—CH$_3$), 2.35 (s,3H,Ar—CH$_3$), 3.10 (d,2H,CH$_2$—P) $J_{PH} = 22$ Hz, 3.16 (q,12H,N—CH$_2$—CH$_3$), 7.26 (s-broad, 4H,Ar—H).

EXAMPLE 15

Preparation of diethyl 4-chlorobenzylphosphonate (P)

The process is as in Example 2. 4-Chlorobenzyl bromide was used instead of 3-bromobenzyl bromide. Yield: 78%; boiling point: 123° C./0.4 mm; $^1$H-NMR (60 MHz, CDCl$_3$/TMS): $\delta = 1.25$ (t, 6H, P—O—CH$_2$—CH$_3$); 3.10 (d,2H,CH$_2$—P) $J_{PH} = 22$ Hz, 4.05 (dq,4H,P—O—CH$_2$—CH$_3$), 7.30 (s,4H,Ar—H)

EXAMPLE 16

Preparation of diethyl 2-iodobenzylphosphonate (R)

The process is as in Example 2. 2-Iodobenzyl bromide was used instead of 3-bromobenzyl bromide. Yield: 69%; boiling point: 113° C./0.1 mm;

$^1$H-NMR (60 MHz, CDCl$_3$/TMS): $\delta = 1.30$ (t,6H,P—O—CH$_2$—CH$_3$), 3.57 (d,2H,CH$_2$—P) $J_{PH} = 21$ Hz, 4.10 (dq,4H,P—O—CH$_2$—CH$_3$), 6.80–8.03 (m,4H,Ar—H).

EXAMPLE 17

Preparation of diethyl 4-fluorobenzylphosphonate (S)

The process is as in Example 2. 4-Fluorobenzyl bromide was used instead of 3-bromobenzyl bromide. Yield: 84%; boiling point: 90° C./0.25 mm; $^1$H-NMR (60 MHz, CDCl$_3$/TMS): $\delta = 1.30$ (t,6H, P—O—CH$_2$—CH$_3$), 3.13 (d,2H,CH$_2$—P) $J_{PH} = 22$ Hz, 4.07 (dq,4H, P—O—CH$_2$—CH$_3$), 6.85–7.53 (m,4H,Ar—H).

EXAMPLE 18

Preparation of diisopropyl 4-iodobenzylphosphonate (T)

The process is as in Example 11. 4-Iodobenzyl bromide was used instead of 2-methylbenzyl bromide. Yield: 78%; boiling point: 137° C./0.1 mm;

$^1$H-NMR (60 MHz, CDCl$_3$/TMS): $\delta = 1.20$ (t,6H,P—O—CH(C$_3$)$_2$), 3.05 (d,2H,CH$_2$—P) $J_{PH} = 22$ Hz, 4.60 (dhep,2H,P—O—CH(CH$_3$)$_2$), 6.93–7.80 (m,4H,Ar—H).

EXAMPLE 19

Diethyl 2-nitrobenzylphosphonate (U)

The process is as in Example 2; use of 2-nitrobenzyl bromide instead of 3-bromobenzyl bromide.

Yield: 73%; boiling point: 158° C./0.4 torr; $^1$H-NMR (60 MHz, CDCl$_3$/TMS); $\delta = 1.20$ (t,6H,P—O—CH$_2$—CH$_3$); 3.70 (d,2H,P—CH$_2$, $J_{PH} = 23$ Hz); 4.01 (dq, 4H, P—O—CH$_2$—CH$_3$); 7.06–8.10 (m,4H,Ar—H).

EXAMPLE 20

Diethyl 2-phenylethylphosphonate (V)

The process is as in Example 2; use of 1-phenylethyl bromide instead of 3-bromobenzyl bromide.

Yield: 60%; boiling point: 122° C./0.05 torr; $^1$H-NMR (270 MHz, CDCl$_3$/TMS): $\delta = 1.15$ & 1.29 (t,6H,P—O—CH$_2$—CH$_3$); 1.55 & 1.62 (d,3H,CH—CH$_3$); 3.18 (dq,1H,P—CH, $J_{PH} = 23$ Hz); 3.71–4.20 (m,4H,P—O—CH$_2$—CH$_3$); 7.20–7.46 (m,5H,Ar—H).

EXAMPLE 21

Diethyl 2-carboxyethylbenzylphosphonate (W)

82.1 g (0.5 mol) of methyl o-toluate were dissolved in 375 ml of $CCl_4$, and 94 g (0.5 mol) of N-bromosuccinimide (NBS) and 0.3 g of azobisisobutyronitrile (AIBN) were added. The mixture was boiled under reflux for 3 hours, while stirring, and cooled and the succinimide formed was filtered off and rinsed with $CCl_4$. The solvent was evaporated off on a rotary evaporator. The ethyl o-bromomethylbenzoate formed (131.7 g) was further reacted as described under Example 2 without further purification.

Yield: 63%; boiling point: 130° C./0.2 torr; $^1$H-NMR (270 MHz, $CDCl_4$/TMS): $\delta=1.22$ (t,6H,P—O—CH$_2$—CH$_3$); 1.39 (t,3H,C—O—CH$_2$—CH$_3$); 3.41 (d,2H,P—CH$_2$, $J_{PH}=23$ Hz); 3.99 (dq,4H,P—O—CH$_2$—CH$_3$); 4.38 (q,2H,C—O—CH$_2$—CH$_3$); 7.25–7.49 (m,3H,Ar—H); 7.92 (d,1H,Ar—H).

EXAMPLE 22

Diethyl 3-carboxymethylbenzylphosphonate (X)

Methyl m-toluate was brominated with NBS and AIBN as described in Example 21 to give methyl m-bromomethylbenzoate, and this was further reacted with triethyl phosphite as described in Example 2 without further purification.

Yield: 45%; boiling point: 146° C./0.5 torr; $^1$H-NMR (60 MHz, $CDCl_3$/TMS): $\delta=1.25$ (t,6H,P—O—CH$_2$—CH$_3$); 3.21 (d,2H,P—CH$_2$, $J_{PH}=22$ Hz); 3.93 (s,3H,OCH$_3$); 4.02 (dq,4H,P—O—CH$_2$—CH$_3$); 7.25–8.10 (m,4H,Ar—H).

EXAMPLE 23

Diethyl 2-(ethylacetyl)benzylphosphonate (Y)

o-Tolylacetic acid was brominated with NBS and AIBN as described in Example 21 to give ethyl o-bromomethylphenylacetate, and this was reacted with triethyl phosphite as described in Example 2.

Yield: 33%; boiling point: 152° C./0.3 torr; $^1$H-NMR (60 MHz, $CDCl_3$/TMS); $\delta=1.23$ (t,9H,P—O—CH$_2$—CH$_3$ & C—O—CH$_2$—CH$_3$); 3.29 (d,2H,P—CH$_2$, $J_{PH}=22$ Hz); 3.70–4.28 (m,8H,P—O—CH$_2$—CH$_3$ & C—O—CH$_2$CH$_3$ & Ar—CH$_2$—C(O)); 7.30 (s,4H,Ar—H).

EXAMPLE 24

Diethyl 4-methoxybenzylphosphonate (Z)

p-Methoxybenzyl chloride was reacted with triethyl phosphite as described in Example 2.

Yield: 88%; boiling point: 127° C./0.2 torr; $^1$H-NMR (270 MHz, $CDCl_3$/TMS): $\delta=1.25$ (t,6H,P—O—CH$_2$—CH$_3$); 3.11 (d,2H,P—CH$_2$, $J_{PH}=23$ Hz); 3.80 (s,3H,OCH$_3$); 4.07 (dq,4H,P—O—CH$_2$—CH$_3$); 6.73–7.32 (m,4H,Ar—H).

EXAMPLE 25

Diethyl 2-methyl-4-bromobenzylphosphonate (AA)

10 g (42 mmol) of diethyl 2-methylbenzylphosphonate were dissolved in 60 ml of trimethyl phosphate and the solution was introduced into a flask protected from light and moisture. 16 g (0.05 mol) of $Br_2$ were added dropwise, while stirring. The mixture was stirred at 90° C. for 15 hours and, after cooling, was diluted with 100 ml of water and extracted three times with 100 ml of n-hexane each time. The organic phase wa dried, concentrated and distilled.

Yield: 35%; boiling point: 124° C./0.2 mm; $^1$H-NMR (60 MHz, $CDCl_3$/TMS): $\delta=1.25$ (t,6H,P—O—CH$_2$—CH$_3$); 2.30 (s,3H,Ar—CH$_3$); 3.17 (d,2H,P—CH$_2$, $J_{PH}=23$ Hz); 4.06 (dq,4H,P—O—CH$_2$—CH$_3$); 6.93–7.88 (m,3H,Ar—H).

EXAMPLE 26

Diethyl 4-trifluoromethylbenzylphosphate (AB)

10 g (0.056 mol) of 4-trifluoromethylbenzyl alcohol were mixed with 13.5 g (0.114 mol) of $SOCl_2$ and the mixture was boiled under reflux for five hours. Excess $SOCl_2$ was distilled off. The 4-trifluorometnhylbenzyl chloride formed was reacted with triethyl phosphite as described in Example 2 without further purification.

Yield: 48%; boiling point: 90° C./0.45 torr; $^1$H-NMR (60 MHz, $CDCl_3$/TMS): $\delta=1.27$ (t,6H,P—O—CH$_2$—CH$_3$); 3.21 (d,2H,P—CH$_2$, $J_{PH}=23$ Hz); 4.10 (dq,4H,P—O—CH$_2$—CH$_3$); 7.27–7.77 (m,4H,Ar—H).

EXAMPLE 27

1,2-Phenylene-bis(diethyl methylphosphonate) (AC)

1,2-dibromomethylbenzene was reacted with two equivalents of triethyl phosphite as described in Example 2.

Yield: 68%; boiling point: 161° C./0.15 torr; $^1$H-NMR (270 MHz, $CDCl_3$/TMS): $\delta=1.25$ (t,12H,P—O—CH$_2$—CH$_3$); 3.43 (d,4H,P—CH$_2$, $J_{PH}=21$ Hz); 4.00 (dq,8H,P—O—CH$_2$—CH$_3$); 7.16–7.32 (m,4H,Ar—H).

EXAMPLE 28

1,3-Phenylene-bis(diethyl methylphosphonate) (AD)

1,3-Dibromomethylbenzene was reacted with two equivalents of triethyl phosphite as described in Example 2.

Yield: 63%; boiling point: 165°–169° C./0.1 torr; $^1$H-NMR (60 MHz, $CDCl_3$/TMS): $\delta=1.27$ (t,12H,P—O—CH$_2$—CH$_3$); 3.16 (d,4H,P—CH$_2$, $J_{PH}=24$ Hz); 4.07 (dq,8H,P—O—CH$_2$—CH$_3$); 7.25 (s,4H,Ar—H).

EXAMPLE 29

Diethyl 2-carboxybenzylphosphonate (AE)

4 g of diethyl 2-methylbenzylphosphonate were added to a solution of 12 g of $KMnO_4$ and 4 g of $Na_2CO_3$ in 300 ml of water and the mixture was boiled under reflux for 24 hours. It was acidified with 15 ml of concentrated $H_2SO_4$ and extracted five times with 300 ml of ether each time. The organic phase was dried over $MgSO_4$, the solvent was evaporated off on a rotary evaporator and the residue was chromatographed over silica gel ($CH_2Cl_2$/methanol/triethylamine 9/1/0.1).

Yield: 20%; $^1$H-NMR (270 MHz, DMSO/TMS); $\delta=1.13$ (t,6H,P—O—CH$_2$—CH$_3$); 3.29 (d,2H,P—CH$_2$, $J_{PH}=23$ Hz); 3.90 (dq,4H,P—O—CH$_2$—CH$_3$); 7.38–7.88 (m,4H,Ar—H).

EXAMPLE 30

2-Carboxybenzylphosphonic acid (AF)

100 ml of ¾ concentrated HCl were added to 5 g of diethyl 2-carboxyethylbenzylphosphonate and the mixture was heated under reflux for 5 hours. The product crystallized out on cooling.

Yield: 50%; melting point: 209° C.; $^1$H-NMR (60 MHz, D$_2$O/TMS): $\delta=3.66$ (d,2H,P—CH$_2$, J$_{PH}$=23 Hz); 7.21-8.07 (m,4H,Ar—H).

EXAMPLE 31 di-Triethylammonium 2-carboxyethylbenzylphosphonate (AG)

The process is as in Example 14. Diethyl 2-carboxyethylbenzylphosphonate was used instead of diethyl 2-methylbenzylphosphonate.

Yield: 60%; resin; $^1$H-NMR (270 MHz, D$_2$O/TMS): $\delta=1.28$ (t,18H,N—CH$_2$—CH$_3$); 1.39 (t,3H,O—CH$_2$—CH$_3$); 3.19 (q,12H,N—CH$_2$—CH$_3$); 3.50 (d,2H,P—CH$_2$, J$_{PH}$=21 Hz); 4.49 (q,2H,O—CH$_2$—CH$_3$); 7.31-7.83 (m,4H,Ar—H).

EXAMPLE 32

Diethyl 1-methylnaphthylphosphonate (AN)

The process is as in Example 2; use of 1-chloromethylnaphthalene instead of 3-bromobenzyl bromide.

Yield: 71%; boiling point: 150°-155° C./0.15 torr; $^1$H-NMR (270 MHz, CDCl$_3$/TMS); $\delta=1.15$ (t,6H,P—O—CH$_2$—CH$_3$); 3.65 (d,2H,P—CH$_2$, J$_{PH}$=23 Hz); 3.94 (dq,4H,P—O—CH$_2$—CH$_3$); 7.39-8.15 (m,7H,Ar—H).

EXAMPLE 33

Diethyl 2-methylnaphthylphosphonate (AH)

The process is as in Example 2; use of 2-bromomethylnaphthalene instead of 3-bromobenzyl bromide.

Yield: 67%; boiling point: 165°-170° C./0.15 torr; $^1$H-NMR (60 MHz, CDCl$_3$/TMS): $\delta=1.23$ (t,6H,P—O—CH$_2$—CH$_3$); 3.32 (d,2H,P—CH$_2$, J$_{PH}$=22 Hz); 4.04 (dq,4H,P—O—CH$_2$—CH$_3$); 7.28-8.07 (m,7H,Ar—H).

EXAMPLE 34

Diethyl 2-cyanobenzylphosphonate (AK)

The process is as in Example 2; use of 2-bromomethylbenzonitrile instead of 3-bromobenzyl bromide.

Yield: 44%; boiling point: 154° C./0.1 torr; $^1$H-NMR (60 MHz, CDCl$_3$/TMS): $\delta=1.30$ (t,6H,P—O—CH$_2$—CH$_3$); 3.41 (d,2H,P—CH$_2$, J$_{PH}$=22 Hz); 4.13 (dq,4H,P—O—CH$_2$—CH$_3$); 7.17-7.86 (m,4H,Ar—H).

EXAMPLE 35

Diethyl 4-cyanobenzylphosphonate (AL)

The process is as in Example 2; use of 4-bromomethylbenzonitrile instead of 3-bromobenzyl bromide.

Yield: 44%; boiling point: 154° C./0.1 torr; $^1$H-NMR (60 MHz, CDCl$_3$/TMS): $\delta=1.25$ (t,6H,P—O—CH$_2$—CH$_3$); 3.20 (d,2H,P—CH$_2$, J$_{PH}$=22 Hz); 4.05 (dq,4H,P—O—CH$_2$—CH$_3$); 6.98-7.71 (m,4H,Ar—H).

EXAMPLE 36

2-Methylbenzylphosphonic acid (AM)

The process is as in Example 28. Diethyl 2-methylbenzylphosphonate is used instead of diethyl 2-carboxyethylbenzylphosphonate.

Yield: 77%; melting point: 199° C.; $^1$H-NMR (270 MHz, DMSO/TMS): $\delta=2.32$ (s,3H,CH$_3$); 2.95 (d,2H,P—CH$_2$, J$_{PH}$=22 Hz); 7.03-7.22 (m,4H,Ar—H).

EXAMPLE 37

Pathogen-free NMRI mice (NMRI: Naval Medical Research Institute) weighing about 15 g were infected intraperitoneally with herpes simplex type 1 and then treated intraperitoneally, subcutaneously or orally with the compounds mentioned in Table 1. The treatment was performed twice daily, starting after the infection. The substances were administered to the experimental animals 5 or 9 times (see Table 1). The treatment success was determined from the disease course and the survival rate in comparison with the untreated control animals. These animals were given an administration of a water-soluble methyl hydroxyethyl cellulose (viscosity 300 Pa.s in 2% strength solution) instead of the compound to be tested. The experiments were performed on groups of 5 mice each per substance.

The chemotherapeutic action can be seen from Table 1.

TABLE 1

| | Herpes simplex 1 | | |
|---|---|---|---|
| Substance | Dosage (mg/kg) | Survivors | Average survival time (days) |
| A | po 5 × 2.5 | 3 | 10.5 |
| A | po 5 × 25 | 3 | 9.0 |
| Control | po 5 × 0 | 2 | 9.7 |
| A | sc 5 × 2.5 | 2 | 12.0 |
| A | sc 5 × 25 | 4 | 9.0 |
| A | sc 5 × 250 | 4 | 9.0 |
| Control | sc 5 × 0 | 1 | 7.5 |
| C | po 5 × 2.5 | 2 | 6.7 |
| C | po 5 × 25 | 3 | 8.5 |
| C | po 5 × 250 | 2 | 8.0 |
| Control | po 5 × 0 | 2 | 8.0 |
| D | po 5 × 0.25 | 2 | 8.7 |
| D | po 5 × 2.5 | 2 | 7.0 |
| D | po 5 × 25 | 3 | 6.0 |
| Control | po 5 × 0 | 0 | 8.0 |
| D | po 9 × 3.0 | 4 | 8.0 |
| D | po 9 × 10.0 | 2 | 8.3 |
| D | po 9 × 30.0 | 3 | 10.5 |
| Control | po 9 × 0 | 1 | 7.5 |
| D | sc 5 × 0.25 | 1 | 9.0 |
| D | sc 5 × 2.5 | 3 | 8.5 |
| D | sc 5 × 25 | 4 | 8.0 |
| Control | sc 5 × 0 | 1 | 7.7 |
| E | po 9 × 3 | 1 | 5.7 |
| E | po 9 × 0 | 2 | 7.0 |
| E | po 9 × 30 | 3 | 7.5 |
| Control | po 9 × 0 | 2 | 7.0 |
| E | sc 9 × 3 | 1 | 6.3 |
| E | sc 9 × 10 | 3 | 6.5 |
| E | sc 9 × 30 | 2 | 6.7 |
| Control | sc 9 × 0 | 1 | 8.3 |
| K | sc 5 × 2.5 | 0 | 7.4 |
| K | sc 5 × 25 | 0 | 8.6 |
| K | sc 5 × 250 | 3 | 8.0 |
| Control | sc 5 × 0 | 0 | 7.0 |
| L | po 5 × 2.5 | 5 | — |
| L | po 5 × 25 | 2 | 8.7 |
| L | po 5 × 250 | 2 | 8.7 |
| Control | po 5 × 0 | 2 | 9.7 |
| L | sc 5 × 2.5 | 1 | 8.3 |
| L | sc 5 × 25 | 0 | 7.4 |
| L | sc 5 × 250 | 3 | 6.5 |
| Control | sc 5 × 0 | 1 | 7.5 |
| M | sc 5 × 2.5 | 4 | 7.0 |
| M | sc 5 × 25 | 3 | 7.5 |
| M | sc 5 × 250 | 1 | 7.7 |
| Control | sc 5 × 0 | 1 | 7.5 |
| W | po 9 × 3.0 | 1 | 8.5 |
| W | po 9 × 10 | 1 | 9.5 |
| W | po 9 × 30 | 4 | 8.0 |
| Control | po 9 × 0 | 1 | 8.7 | po = oral
sc = subcutaneous

EXAMPLE 38

Cell cultures of Hela and Vero cells were transinoculated in microtiter plates and infected with myxoviruses (influenza A2). 2 hours after the infection, the compound (O) was added to the infected cell cultures in various dilutions. 49 to 72 hours after the infection, the therapeutic success was determined microscopically from the cytopathogenic effect and photometrically from neutral red images (Finter stain test, N. B. Finter, Interferons, North Holland Publishing Co., Amsterdam, 1966). The minimum concentration at which about half the infected cells show no cytopahtogenic effect is regarded as the minimum inhibitory concentration (MIC). The results are summarized in Table 2.

TABLE 2

| Substance | Influenza A2 | |
|---|---|---|
| | MIC (µg/ml) | DTM (µg/ml) |
| 0 | 14.8 | 133.3 |

DTM = dosis tolerata maxima (maximum tolerated dose)

EXAMPLE 39

Pathogen-free NMRI mice weighing about 16 g were infected intranasally with influenza A2 and then treated subcutaneously or orally with the compounds mentioned in Table 3. Amantadine was always used as comparison. The treatment was performed twice daily for 2.5 days, starting after the infection. The treatment success was determined from the disease course and the survival rate in comparison with the untreated control animals. These animals were given an administration of a water-soluble methyl hydroxyethyl cellulose (viscosity 300 Pa.s in 2% strength solution) instead of the substance to be tested. The experiments were performed on groups of 5 mice each per substance.

The chemotherapeutic action is shown in Table 3.

TABLE

| Substance | Influenza A2 | | |
|---|---|---|---|
| | Dosage (mg/kg) | Survivors | Average survival time (days) |
| Control | po 0.0 | 2 | 7.7 |
| amantadine | po 80.0 | 5 | — |
| A | po 0.25 | 3 | 6.0 |
| A | po 2.5 | 4 | 7.0 |
| A | po 25.0 | 5 | — |
| Control | sc 0.0 | 1 | 6.5 |
| amantadine | sc 80.0 | 5 | — |
| A | sc 0.25 | 2 | 7.0 |
| A | sc 2.5 | 4 | 7.0 |
| A | sc 25.0 | 3 | 7.0 |
| Control | po 0.0 | 1 | 7.0 |
| C | po 0.25 | 1 | 8.0 |
| C | po 2.5 | 4 | 8.0 |
| C | po 25 | 4 | 7.0 |
| Control | po 0.0 | 1 | 7.7 |
| amantadine | po 80.0 | 5 | — |
| D | po 0.25 | 4 | 8.0 |
| D | po 2.5 | 5 | — |
| D | po 25.0 | 5 | — |
| Control | sc 0.0 | 0 | 7.4 |
| amantadine | sc 80.0 | 5 | — |
| D | sc 0.25 | 4 | 7.0 |
| D | sc 2.5 | 2 | 8.0 |
| D | sc 25.0 | 4 | 7.0 |
| Control | po 0.0 | 2 | 7.3 |
| amantadine | po 80.0 | 5 | — |
| E | po 2.5 | 5 | — |
| E | po 25.0 | 5 | — |
| E | po 250.0 | 2 | 2.3 |
| Control | sc 0.0 | 0 | 6.6 |
| amantadine | sc 80.0 | 5 | — |
| E | sc 2.5 | 3 | 7.0 |
| E | sc 25.0 | 2 | 6.3 |
| E | sc 250.0 | 0 | toxic |
| Control | po 0.0 | 2 | 6.7 |
| G | po 0.25 | 5 | — |
| G | po 2.5 | 3 | 6.5 |
| G | po 25 | 1 | 7.7 |
| Control | po 0.0 | 2 | 6.7 |
| H | po 0.25 | 3 | 5.5 |
| H | po 2.5 | 4 | 8.0 |
| H | po 25 | 3 | 8.5 |
| Control | po 0.0 | 2 | 6.7 |
| I | po 0.25 | 3 | 6.5 |
| I | po 2.5 | 4 | 6.0 |
| I | po 25 | 3 | 7.0 |
| Control | po 0.0 | 2 | 6.7 |
| K | po 0.25 | 4 | 6.0 |
| K | po 2.5 | 2 | 7.0 |
| K | po 25 | 3 | 6.5 |
| Control | po 0.0 | 2 | 7.7 |
| amantadine | po 80.0 | 5 | — |
| L | po 0.25 | 4 | 8.0 |
| L | po 2.5 | 3 | 6.0 |
| L | po 25.0 | 5 | — |
| Control | sc 0.0 | 1 | 6.5 |
| amantadine | sc 80.0 | 5 | — |
| L | sc 0.25 | 3 | 9.5 |
| L | sc 2.5 | 0 | 6.8 |
| L | sc 25.0 | 4 | 10.0 |
| Control | po 0.0 | 2 | 8.3 |
| amantadine | po 80.0 | 5 | — |
| M | po 0.25 | 4 | 7.0 |
| M | po 2.5 | 4 | 7.0 |
| M | po 25.0 | 5 | — |
| Control | sc 0.0 | 1 | 6.5 |
| M | sc 0.25 | 5 | — |
| M | sc 2.5 | 3 | 7.0 |
| M | sc 25 | 5 | — |
| Control | po 0.0 | 0 | 6.6 |
| N | po 0.25 | 4 | 8.0 |
| N | po 2.5 | 3 | 8.0 |
| N | po 25 | 3 | 6.5 |
| Control | po 0.0 | 0 | 7.2 |
| O | po 0.25 | 5 | — |
| O | po 2.5 | 3 | 8.5 |
| O | po 25 | 3 | 9.0 |
| Control | po 0.0 | 1 | 7.0 |
| P | po 0.25 | 3 | 8.5 |
| P | po 2.5 | 4 | 7.0 |
| P | po 25 | 3 | 6.5 |
| Control | sc 0.0 | 0 | 6.4 |
| R | sc 0.25 | 3 | 9.0 |
| R | sc 2.5 | 4 | 7.0 |
| R | sc 25 | 0 | 6.8 |
| Control | sc 0.0 | 0 | 6.4 |
| T | sc 0.25 | 3 | 7.0 |
| T | sc 2.5 | 4 | 8.0 |
| T | sc 25 | 4 | 7.0 |
| Control | sc 0.0 | 1 | 8.5 |
| U | sc 0.25 | 4 | 7.0 |
| U | sc 2.5 | 4 | 7.0 |
| U | sc 25 | 2 | 7.3 |
| Control | po 0.0 | 1 | 7.0 |
| V | po 0.25 | 4 | 7.0 |
| V | po 2.5 | 3 | 9.0 |
| V | po 25 | 3 | 7.5 |
| Control | po 0.0 | 2 | 7.0 |
| W | po 2.5 | 4 | 9.0 |
| W | po 25 | 4 | 9.0 |
| W | po 250 | 3 | 7.0 |
| Control | po 0.0 | 0 | 6.6 |
| X | po 0.25 | 3 | 7.0 |
| X | po 2.5 | 4 | 6.0 |
| Control | po 0.0 | 2 | 8.3 |
| Y | po 0.25 | 2 | 8.3 |
| Y | po 2.5 | 2 | 6.7 |
| Y | po 25 | 4 | 8.0 |
| Control | po 0.0 | 0 | 7.4 |
| Z | po 0.25 | 3 | 7.0 |
| Z | po 2.5 | 4 | 7.0 |
| Z | po 25 | 1 | 7.3 |
| Control | po 0.0 | 0 | 7.4 |
| AB | po 0.25 | 4 | 9.0 |

TABLE -continued

| Substance | Influenza A2 Dosage (mg/kg) | Survivors | Average survival time (days) |
|---|---|---|---|
| AB | po 2.5 | 4 | 6.0 |
| AB | po 25 | 1 | 7.5 |
| Control | sc 0.0 | 0 | 6.2 |
| AC | sc 0.25 | 2 | 6.3 |
| AC | sc 2.5 | 1 | 7.0 |
| AC | sc 25 | 4 | 6.0 |
| Control | sc 0.0 | 0 | 6.4 |
| AD | sc 0.25 | 2 | 7.0 |
| AD | sc 2.5 | 3 | 6.5 |
| AD | sc 25 | 4 | 7.0 |
| Control | po 0.0 | 2 | 7.7 |
| amatadine | po 80 | 5 | — |
| AE | po 0.25 | 2 | 7.0 |
| AE | po 2.5 | 4 | 7.0 |
| AE | po 25 | 5 | — |
| Control | po 0.0 | 0 | 7.2 |
| AF | po 0.25 | 4 | 10.0 |
| AF | po 2.5 | 5 | — |
| AF | po 25 | 0 | 7.2 |
| Control | po 0.0 | 2 | 6.7 |
| AH | po 0.25 | 4 | 9.0 |
| AH | po 2.5 | 3 | 7.0 |
| AH | po 25 | 2 | 8.0 |
| Control | po 0.0 | 2 | 8.7 |
| AL | po 0.25 | 0 | 8.0 |
| AL | po 2.5 | 2 | 7.3 |
| AL | po 25 | 5 | — | po = oral
sc = subcutaneous

EXAMPLE 40

Laboratory mice (NMRI, female, weight 20 to 24 g) were infected intravenously with mouse serum containing Friend leukemia virus (FLV). A 10-day treatment started 48 hours after the infection. The mice were treated with the substances listed in Table 4. The substances listed were administered orally or intraperitoneally once per day. 14 days after infection, the animals were sacrificed by cervical dislocation and the spleens were removed. The weight of the spleens was determined. The spleen weight of the treated animals were compared with that of the untreated control animals as a measurement parameter of the therapeutic efficacy.

Suramin and azidothymidine (AZT) were used as standard substances. The action of the substances can be seen from Table 4.

TABLE 4

| Substance | Dosage (mg/kg) | FLV Survival rate (%) | Relative spleen weight (%) |
|---|---|---|---|
| Control | po 0.0 | 100 | 12.36 |
| AZT | po 15.5 | 100 | 3.26 |
| E | po 16.5 | 100 | 6.94 |
| E | po 77.5 | 100 | 8.54 |
| Control | ip 0.0 | 100 | 8.80 |
| E | ip 50.0 | 90 | 4.83 |
| Control | po 0.0 | 100 | 12.36 |
| AZT | po 15.5 | 100 | 3.26 |
| C | po 16.0 | 100 | 6.5 |
| C | po 75.0 | 100 | 6.47 |
| Control | ip 0.0 | 100 | 8.08 |
| suramin | ip 50.0 | 100 | 6.70 |
| C | ip 50.0 | 100 | 6.55 |
| Control | po 0.0 | 100 | 10.50 |
| AZT | po 14.5 | 100 | 1.81 |
| A | po 15.0 | 100 | 6.93 |
| A | po 73.5 | 100 | 6.15 |
| Control | ip 0.0 | 100 | 10.50 |
| suramin | ip 50.0 | 100 | 6.17 |
| A | ip 50.0 | 100 | 7.22 |
| Control | ip 0.0 | 100 | 10.42 |
| suramin | ip 50.0 | 60 | 4.12 |
| B | ip 50.0 | 80 | 6.60 |
| Control | ip 0.0 | 100 | 10.50 |
| suramin | ip 50.0 | 100 | 6.17 |
| M | ip 50.0 | 90 | 7.46 |
| Control | ip 0.0 | 100 | 8.52 |
| AZT | ip 50 | 100 | 5.40 |
| O | ip 30 | 90 | 5.06 |
| O | ip 10 | 90 | 6.32 |
| Control | ip 0.0 | 100 | 10.42 |
| suramin | ip 50 | 60 | 4.12 |
| U | ip 50 | 90 | 7.56 |
| Control | po 0.0 | 100 | 11.36 |
| AZT | po 18.0 | 100 | 6.42 |
| K | po 15.5 | 90 | 9.02 | po = oral
ip = intraperitoneal

We claim:
1. A method for the treatment of diseases caused by DNA viruses or RNA viruses comprising administering to a host suffering from said diseases an effective amount of a compound of the formula I

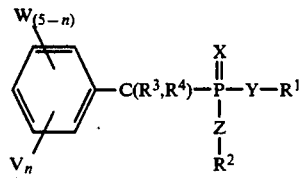

in which
V is a straight-chain or branched alkyl group having 1 to 4 carbon atoms, fluorine, chlorine, bromine, iodine or hydrogen,
n is an integer from 1 to 5,
W is a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, a straight-chain or branched alkoxy group having 1 to 10 carbon atoms, an aryl group having 6, 10 or 14 carbon atoms, or is an alkyl group having 1 to 4 carbon atoms which is substituted by one or more substituents from the group consisting of a radical of the formula —COOR$^6$, chlorine, bromine, iodine, fluorine, a fused-on aromatic and said fused-on aromatic which is substituted by an alkyl group having 1 to 4 carbon atoms, cyanide, nitro or hydrogen, or is a radical of the formula Ia —COOR$^6$  Ia in which
R$^6$ is a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, sodium, potassium, calcium, magnesium, aluminum, lithium, ammonium, triethylammonium, hydrogen or a straight-chain or branched halogenoalkyl group having 1 to 20 carbon atoms, in which halogen is chlorine, bromine, iodine or fluorine, R¹ and R², which can be identical or different, are a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, sodium, potassium, calcium, magnesium, aluminum, lithium, ammonium, triethylammonium, hydrogen or a straight-chain or branched halogenoalkyl group having 1 to 20 carbon atoms, in which halogen is chlorine, bromine, iodine or fluorine, R³ and R⁴, which are identical or different, are a straight-chain or branched alkyl group having 1 to 20 carbon atoms, a straight-chain or branched alkynyl or alkenyl group having 2 to 20 carbon atoms, a cycloalkyl group having 3 to 8 carbon atoms, an aralkyl group having 7 to 20 carbon atoms, a straight-chain or branched alkoxy group having 1 to 10 carbon atoms, hydrogen, fluorine, chlorine, bromine or iodine, or are a radical of the formula Ib —COOR⁷     Ib in which
R⁷ is a straight-chain or branched alkyl group having 1 to 4 carbon atoms and
X, Y and Z, which are identical or different, are oxygen or sulfur.

2. The method as claimed in claim 1,
in which in the compound of the formula I
V is bromine, hydrogen or methyl,
n is an integer from 1 to 5,
W is methoxy or hydrogen,
R¹ and R², which are identical or different, are a straight-chain or branched alkyl group having 1 to 10 carbon atoms, an alkenyl or alkynyl group having 2 to 10 carbon atoms, an aralkyl group having 7 to 16 carbon atoms or hydrogen,
R³ and R⁴, which are identical or different, are a straight-chain or branched alkyl group having 1 to 4 carbon atoms, an alkenyl or alkynyl group having 2 to 10 carbon atoms, a straight-chain or branched alkoxy group having 1 to 4 carbons atoms, hydrogen, fluorine, chlorine or bromine, or are a radical of the formula Ib —COOR⁷     Ib in which
R⁷ is a straight-chain or branched alkyl group having 1 to 4 carbon atoms and
X, Y and Z are oxygen.

3. A method for the treatment of diseases caused by DNA viruses or RNA viruses comprising administering to a host suffering from said diseases a pharmaceutical composition which comprises an effective amount of a compound of the formula I

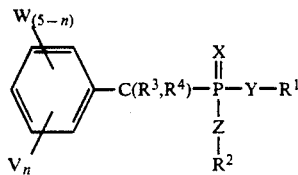

in which

V is a straight-chain or branched alkyl group having 1 to 4 carbon atoms, fluorine, chlorine, bromine, iodine or hydrogen,
n is an integer from 1 to 5,
W is a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, a straight-chain or branched alkoxy group having 1 to 10 carbon atoms, an aryl group having 6, 10 or 14 carbon atoms, or is an alkyl group having 1 to 4 carbon atoms which is substituted by one or more substituents from the group consisting of a radical of the formula —COOR⁶, chlorine, bromine, iodine, fluorine, a fused-on aromatic and said fused-on aromatic which is substituted by an alkyl group having 1 to 4 carbon atoms, cyanide, nitro or hydrogen, or is a radical of the formula Ia —COOR⁶     Ia in which
R⁶ is a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, sodium, potassium, calcium, magnesium, aluminum, lithium, ammonium, triethylammonium, hydrogen or a straight-chain or branched halogenoalkyl group having 1 to 20 carbon atoms, in which halogen is chlorine, bromine, iodine or fluorine,
R¹ and R², which can be identical or different, are a straight-chain or branched alkyl group having 1 to 20 carbon atoms, a straight-chain or branched alkenyl or alkynyl group having 2 to 20 carbon atoms, an aralkyl group having 7 to 20 carbon atoms, a cycloalkyl group having 3 to 8 carbon atoms, sodium, potassium, calcium, magnesium, aluminum, lithium, ammonium, triethylammonium, hydrogen or a straight-chain or branched halogenoalkyl group having 1 to 20 carbon atoms, in which halogen is chlorine, bromine, iodine or fluorine,
R³ and R⁴, which are identical or different, are a straight-chain or branched alkyl group having 1 to 20 carbon atoms, a straight-chain or branched alkynyl or alkenyl group having 2 to 20 carbon atoms, a cycloalkyl group having 3 to 8 carbon atoms, an aralkyl group having 7 to 20 carbon atoms, a straight-chain or branched alkoxy group having 1 to 10 carbon atoms, hydrogen, fluorine, chlorine, bromine or iodine, or are a radical of the formula Ib —COOR⁷     Ib in which
R⁷ is a straight-chain or branched alkyl group having 1 to 4 carbon atoms and
X, Y and Z, which are identical or different, are oxygen or sulfur,
together with a physiologically tolerated excipient.

4. A method as claimed in claim 3,
in which in the compound of the formula I
V is bromine, hydrogen or methyl,
n is an integer from 1 to 5,
W is methoxy or hydrogen, $R^1$ and $R^2$, which are identical or different, are a straight-chain or branched alkyl group having 1 to 10 carbon atoms, an alkenyl or alkynyl group having 2 to 10 carbon atoms, an aralkyl group having 7 to 16 carbon atoms or hydrogen, $R^3$ and $R^4$, which are identical or different, are a straight-chain or branched alkyl group having 1 to 4 carbon atoms, an alkenyl or alkynyl group having 2 to 10 carbon atoms, a straight-chain or branched alkoxy group having 1 to 4 carbons atoms, hydrogen, fluorine, chlorine or bromine, or are a radical of the formula Ib $$-COOR^7 \qquad \text{Ib}$$

in which $R^7$ is a straight-chain or branched alkyl group having 1 to 4 carbon atoms and X, Y and Z are oxygen.

* * * * *